United States Patent
Takeuchi

(10) Patent No.: US 6,994,872 B2
(45) Date of Patent: Feb. 7, 2006

(54) MONOLAYER SUGAR-COATED TABLET AND PROCESS FOR PREPARATION THEREOF

(75) Inventor: Toshio Takeuchi, Yokohama (JP)

(73) Assignee: Teikoku Hormone Mfg. Co., Ltd., Tokyo (JP)

(*) Notice: Subject to any disclaimer, the term of this patent is extended or adjusted under 35 U.S.C. 154(b) by 0 days.

(21) Appl. No.: 09/795,083

(22) Filed: Mar. 1, 2001

(65) Prior Publication Data

US 2002/0044970 A1 Apr. 18, 2002

(30) Foreign Application Priority Data

Aug. 31, 2000 (JP) .............................. 2000-262774

(51) Int. Cl.
  *A61K 9/36* (2006.01)
  *A61K 9/00* (2006.01)
  *A61K 9/20* (2006.01)
  *A61K 9/28* (2006.01)

(52) U.S. Cl. ...................... 424/479; 424/400; 424/464; 424/474; 424/475

(58) Field of Classification Search ................ 424/464, 424/474, 475, 479, 400, 465
See application file for complete search history.

(56) References Cited

U.S. PATENT DOCUMENTS

| | | | | |
|---|---|---|---|---|
| 3,331,696 A | * | 7/1967 | Theel et al. | 106/162.1 |
| 4,284,638 A | * | 8/1981 | Waldmeier et al. | 514/320 |
| 5,662,936 A | * | 9/1997 | de Haan et al. | 424/479 |
| 6,274,162 B1 | * | 8/2001 | Steffenino et al. | 424/439 |

FOREIGN PATENT DOCUMENTS

| | | | |
|---|---|---|---|
| GB | 1025139 | * | 4/1966 |
| GB | 1086150 | * | 10/1967 |
| JP | 51-70808 | | 6/1976 |
| JP | 56-87518 | | 7/1981 |
| JP | 56-39287 | | 9/1981 |
| JP | 62-000010 | * | 1/1987 |
| JP | 7-17497 | | 3/1995 |
| JP | 9-175997 | | 7/1997 |

OTHER PUBLICATIONS

Collection of Summaries of Lectures at the 120th Annual Meeting (GIFU) of the Pharmaceutical Society of Japan, (2000), with English translation.

* cited by examiner

*Primary Examiner*—Gary Kunz
*Assistant Examiner*—Sharmila S Gollamudi
(74) *Attorney, Agent, or Firm*—Wenderoth, Lind & Ponack, L.L.P.

(57) ABSTRACT

This invention relates to a monolayer sugar-coated tablet which is coated with a sugar-coating liquid containing 30–54% by weight of saccharide, 2–10% by weight of polyethylene glycol and 0.2–2% by weight of polyvinylpyrrolidone, and a process for preparing the same.

According to the invention, a monolayer sugar-coated tablet and a process for preparation thereof are provided with very great economical advantages that the skill required for conventional sugar-coating processing is unnecessary and furthermore consumption of sugar-coating material can be reduced and the processing time can be shortened.

5 Claims, No Drawings

MONOLAYER SUGAR-COATED TABLET AND PROCESS FOR PREPARATION THEREOF

BACKGROUND OF THE INVENTION

1. Field of the Invention

This invention relates to monolayer sugar-coated tablet which is coated with single sugar-coating liquid of specific composition and process for preparation thereof. Because the monolayer sugar-coated tablet of the invention is prepared in single step using a single sugar-coating liquid, it does not require the skill and high technical level of artisans which are normally demanded for ordinary sugar-coating processing. Furthermore, it allows reduction in consumption of sugar-coating material and reduction in processing time, and is economically very advantageous.

2. Description of the Prior Art

Sugar-coating has been widely practiced with pharmaceutical formulations not only for imparting regular shapes to sugar-coated tablets to improve the latter's appearance, but also for the purpose of increasing moisture-proof property to prevent deterioration of the coated product and facilitate administration. Whereas, conventional sugar-coating method requires plural steps including sub-coating, smoothing, coloring, finishing and polishing, and hence need many processing hours. Furthermore, skills are essential for the operations and because the composition of sugar-coating liquid used is normally different for each step, formulation and preservation of those liquids cost much labor. Comparing with methods for preparing other formulations, therefore, the method is considerably cost-taking.

Namely, in generally practiced preparation method of a sugar-coated tablet, first in the sub-coating step uncoated tablets are coated with a sugar-coating liquid whose chief components are saccharide, additives and binder, several tens of times to round the angular portions of the uncoated tablets; then coated with a sugar-coating liquid containing less amount of the additives and having an increased concentration of saccharide several times in the smoothing step, to smooth out the sub-coated layer surface. If necessary the tablets are then sent to a coloring step, wherein they are coated with a pigment-containing sugar-coating liquid several times to be colored, followed by a finishing step in which the surfaces of the tablets are given smoothness suitable for polishing. Finally wax or the like is scattered on the tablets in a polishing step to impart gloss to their surfaces and provide the finished sugar-coated tablet.

Preparation of sugar-coated tablet thus generally requiring complex, multi-step processing and considerably long processing time, attempts to simplify the sugar-coating steps and shorten the processing time have been reported in the past. For example, Laid-open (Kokai) Patent Application Sho 51(1976)-70808A-JP disclosed a sugar-coating method in which sub-coating and/or smoothing steps are dispensed with, by using a sugar-coating liquid obtained by addition of an inorganic high molecular weight substance chiefly of montmorillonite to aqueous solution of sucrose. Kokai Sho 56(1981)-87518A-JP disclosed a preparation process of thin-layer sugar-coated tablets which were spray-coated with about 9 to 40% to the weight of uncoated tablets of a sugar-coating liquid containing about 10–80% by weight of talc to the sugar as suspended in said liquid. Sho 56(1981)-39287B1-JP disclosed a process for making sugar film-coated tablets in which the uncoated tablets were directly coated with a film of a sugar-coating liquid containing at least 10% by weight of polyvinyl alcohol, not more than about 35% by weight of saccharide and an adequate amount of a tackiness-reducing agent. The sugar coatings obtained in those methods, however, are invariably thin, and the sugar-coated tablets obtained thereby cannot fully exhibit the properties characteristic of sugar-coated tablet. Kokai Hei 9(1997)-175997A-JP, furthermore, disclosed a method of coating with a sugar-coating liquid containing 1–4 parts by weight of hydroxypropylmethylcellulose having specific properties and 5–25 parts by weight of a filler formed chiefly of finely pulverized talc. Said process, however, allowed to carry out the sub-coating step and smoothing step using a sugar-coating liquid of identical composition, but the subsequent finishing step and polishing step could not be omitted. Hei 7(1995)-17497B1-JP disclosed a sugar-coating method comprising sprinkling a sugar-coating liquid which contained 40–65% by weight of saccharide and 0.04–1.6% by weight of a surfactant. However, because the sugar-coating liquid used in this method contained the surfactant at such a low ratio, the resulting sugar-coated tablet lacked sufficient smoothness and its gloss also was unsatisfactory.

SUMMARY OF THE INVENTION

The object of the invention is to provide monolayer sugar-coated tablet, and a process for preparation thereof, which are utilizable with high economical advantages because the process does not require skill and high technical level of artisans which are necessary for conventional sugar-coating processing and still enables to decrease consumption of sugar-coating materials and to shorten the processing time.

We have discovered that use of a sugar-coating liquid containing saccharide, polyethylene glycol and polyvinylpyrrolidone at specific ratios enables to carry out the sub-coating, smoothing, coloring and finishing steps without using sugar-coating liquids of different compositions and, furthermore, the polishing step can be dispensed with. We have also found, while it is normally difficult to prepare evenly colored sugar-coated tablet, that colored sugar-coated tablet with good even coloring can be very easily prepared.

Thus, according to the invention, monolayer sugar-coated tablet which is coated with a sugar-coating liquid containing 30–54% by weight of saccharide, 2–10% by weight of polyethylene glycol and 0.2–2% by weight of polyvinylpyrrolidone is provided.

Hereinafter the monolayer sugar-coated tablet and a process for its preparation according to the invention are explained in further details.

DESCRIPTION OF SPECIFIC EMBODIMENTS

In the invention, examples of saccharide useful for the sugar-coating liquid include sucrose, glucose, lactose, sorbitol, mannitol and xylitol. Of those, sucrose is particularly preferred. Concentration of saccharide in the sugar-coating liquid to be used in the invention generally may range 30–54% by weight, preferably 35–45% by weight.

Polyethylene glycol is used for the purpose of increasing extendability of the sugar-coating liquid to uniformize thickness of the coating layer, and preventing deposition of the sugar-coating liquid to pans. Normally polyethylene glycol of average molecular weight ranging from about 1,500 to about 20,000, in particular, from about 7,300 to about 9,300, are conveniently used. The polyethylene glycol concentration in the sugar-coating liquid to be used in the invention may normally range 2–10% by weight, preferably 3–5% by weight.

Polyvinylpyrrolidone which is used as a binder in the sugar-coating liquid according to the invention has an average molecular weight within a range of from about 28,000 to about 1,500,000, in particular, from 1,00,000 to about 1,500,000. It is advantageous to use it at a concentration of 0.2–2% by weight, preferably 0.3–0.5% by weight, to the sugar-coating liquid.

The sugar-coating liquid may additionally contain, as necessity arises, additives which are routinely used for this kind of sugar-coating liquid, e.g., at least one of pigments, calcium carbonate, talc, titanium dioxide, calcium phosphate, calcium sulfate, silicon dioxide, gelatine, pullulan, gum arabic, hydroxypropylcellulose, hydroxypropylmethylcellulose, polyvinyl alcohol, polypropylene glycol, polyoxyethylene-polyoxypropylene glycol and the like, in particular, calcium carbonate and talc. The total concentration of those additives is normally not higher than 40% by weight, preferably within a range of 15–30% by weight, of the sugar-coating liquid.

When colored sugar-coated tablet is desired, evenly colored sugar-coated tablet can be readily prepared by adding an adequate amount of desired pigment(s) to the sugar-coating liquid according to the invention and coating uncoated tablets therewith.

Normally in processing of colored sugar-coated tablet, a pigment-containing colored layer is provided between the smoothed layer and finished layer to prepare colored sugar-coated tablet. However, colored sugar-coated tablets prepared by such conventional process are apt to be not evenly colored due to insufficient thickness of the coloring layer among other reasons. Hence long accumulated experiences and high skill are required to produce evenly colored sugar-coated tablet. Whereas, when the sugar-coating liquid of the invention is used, evenly colored sugar-coated tablet can be prepared with great technical ease, simply by adding any desired pigment to the sugar-coating liquid. Thus the invention is used with particular advantage for making colored sugar-coated tablets.

In the sugar-coating liquid of the invention, the use ratio of the liquid medium, e.g., water, is not critical. Whereas, it can be generally used at a concentration in the order of 30–50% by weight, preferably in the order of 30–33% by weight, to the sugar-coating liquid.

The monolayer sugar-coated tablet of the invention can be produced by coating uncoated tablets with a sugar-coating liquid of the earlier described composition using a sugar-coating apparatus. As the sugar-coating apparatus useful in that occasion, any of those conventionally used in sugar-coating processing can be similarly used, for example, a pair-type or onion-type coating pan, an aerator type coating pan, and the like.

For example, when an onion-type coating pan of 30 cm in inner diameter is used, uncoated tablets are charged in the coating pan, and while rotating the pan at a rate of about 30–45 rpm, a sugar-coating liquid in an amount of about 0.5–4% by weight to the uncoated tablets per application is poured onto the tablets mannually or sprayed with a spray gun, and then air of about 30–60° C. is blown thereinto to dry the tablets. This series of operations is repeated 20 to 50 times, whereby the monolayer sugar-coated tablet of the invention is produced in around 3–8 hours. Furthermore, when the sugar-coating liquid according to the invention is used to make colored sugar-coated tablet, quite surprisingly all the steps from the sub-coating to polishing can be accomplished with a single sugar-coating liquid. Moreover, even when the sugar coating is conducted by manual pouring, evenly colored sugar-coated tablet is obtained.

Thus, according to the invention sugar-coated tablet is produced in single step, without requiring special skill, and economically very excellent effects such as reduction in consumption of sugar-coating material and in processing time are achieved.

EXAMPLES

The invention is hereafter explained in further details, referring to working examples, comparative examples and test examples.

Example 1

Coating was conducted using a sugar-coating liquid formulated by mixing 40 parts of sucrose, 0.4 part of polyvinylpyrrolidone (average molecular weight: 1,000,000–1,500,000), 4 parts of polyethylene glycol 6000, 16 parts of calcium carbonate, 8 parts of talc and 31.6 parts of purified water, the parts being by weight.

About 10,000 uncoated tablets weighing 55 mg/tablet made of lactose, corn starch, polyvinylpyrrolidone (average molecular weight: 28,000–34,000), etc. were put in a stainless steel sugar-coating pan of 30 cm in diameter, and while rotating the pan at a rate of about 36 rpm, 4–10 ml per application of above sugar-coating liquid was applied to the tablets 30 times in total, at about 10 minutes' intervals. The resulting sugar-coated tablet had a shape characteristic of sugar-coated tablets with smooth, glossy surfaces, and had an appearance similar to those polished with wax.

Example 2

Coating was conducted using a sugar-coating liquid formulated by mixing 37.66 parts of sucrose, 0.33 part of polyvinylpyrrolidone (average molecular weight: 1,000,000–1,500,000), 4.18 parts of polyethylene glycol 6000, 16.74 parts of calcium carbonate, 8.17 parts of talc, 0.08 part of food color Red No. 102, 0.17 part of food color Red No. 3 and 32.67 parts of purified water, the parts being by weight.

About 10,000 uncoated tablets weighing 55 mg/tablet made of lactose, corn starch, polyvinylpyrrolidone (average molecular weight: 28,000–34,000), etc. were put in a stainless steel sugar-coating pan of 30 cm in diameter, and while rotating the pan at a rate of about 36 rpm, 4–10 ml per application of above sugar-coating liquid was applied to the tablets 35 times in total, at about 10 minutes' intervals. The resulting red sugar-coated tablet had a shape characteristic of sugar-coated tablets, with evenly colored smooth, lusterous surfaces. The appearance was similar to that of sugar-coated tablets polished with wax. Uneven coloring decreased after 15th coating and eventually became negligible under visual observation.

Example 3

Coating was conducted using a sugar-coating liquid formulated by mixing 40 parts of sucrose, 0.4 part of polyvinylpyrrolidone (average molecular weight: 1,000,000–1,500,000), 4 parts by weight of polyethylene glycol 6000, 16 parts of calcium carbonate, 8 parts of talc, 0.5 part of titanium dioxide, 0.13 part of yellow iron oxide, 0.15 part of iron oxide and 30.82 parts of purified water, the parts being by weight.

About 10,000 uncoated tablets weighing 55 mg/tablet made of lactose, corn starch, polyvinylpyrrolidone (average molecular weight: 28,000–34,000), etc. were put in a stainless steel sugar-coating pan of 30 cm in diameter, and while rotating the pan at a rate of about 36 rpm, 4–10 ml per application of above sugar-coating liquid was applied to the tablets 35 times in total, at about 10 minutes' intervals. The resulting brown sugar-coated tablet had a shape characteristic of sugar-coated tablets, with evenly colored smooth and lusterous surfaces. The appearance was similar to that of sugar-coated tablets polished with wax.

Example 4

Coating was conducted using a sugar-coating liquid formulated by mixing 37.6 parts of sucrose, 0.37 part of polyvinylpyrrolidone (average molecular weight: 1,000,000–1,500,000), 4.03 parts of polyethylene glycol 6000, 16 parts of calcium carbonate, 8 parts of talc, 0.5 part of titanium dioxide, 0.5 part of yellow iron oxide and 33 parts of purified water, the parts being by weight.

About 10,000 uncoated tablets weighing 55 mg/tablet made of lactose, corn starch, polyvinylpyrrolidone (average molecular weight: 28,000–34,000), etc. were put in a stainless steel sugar-coating pan of 30 cm in diameter, and while rotating the pan at a rate of about 36 rpm, 4–10 ml per application of above sugar-coating liquid was applied to the tablets 35 times in total, at about 10 minutes' intervals. The resulting yellow sugar-coated tablet had a shape characteristic of sugar-coated tablets with smooth, evenly colored and lusterous surfaces, and had an appearance similar to those which were polished with wax.

Example 5

Coating was conducted using a sugar-coating liquid formulated by mixing 30 parts of sucrose, 2 parts of polyvinylpyrrolidone (average molecular weight: 1,000,000–1,500,000), 5 parts of polyethylene glycol 6000, 20 parts of calcium carbonate, 10 parts of talc and 33 parts of purified water, the parts being by weight.

About 10,000 uncoated tablets made of lactose, corn starch, polyvinylpyrrolidone (average molecular weight: 28,000–34,000), etc. were put in a stainless steel sugar-coating pan of 30 cm in diameter, and while rotating the pan at a rate of about 36 rpm, 4–10 ml per application of above sugar-coating liquid was applied to the tablets 25 times in total at about 10 minutes' intervals. The resulting sugar-coated tablet had a shape characteristic of sugar-coated tablets with smooth and lusterous surfaces, and had an appearance similar to those polished with wax.

Example 6

Coating was conducted using a sugar-coating liquid formulated by mixing 54 parts of sucrose, 0.6 part of polyvinylpyrrolidone (average molecular weight: 1,000,000–1,500,000), 2 parts of polyethylene glycol 6000, 10 parts of calcium carbonate, 5 parts of talc and 28.4 parts of purified water, the parts being by weight.

About 10,000 uncoated tablets weighing 55 mg/tablet made of lactose, corn starch, polyvinylpyrrolidone (average molecular weight: 28,000–34,000), etc. were put in a stainless steel sugar-coating pan of 30 cm in diameter, and while rotating the pan at a rate of about 36 rpm, 4–10 ml per application of above sugar-coating liquid was applied to the tablets 25 times in total at 10 minutes' intervals. Thus obtained sugar-coated tablet had a shape characteristics of sugar-coated tablets with smooth and lusterous surfaces, and had an appearance similar to those polished with wax.

Comparative Example 1

(Preparation of Red Sugar-coated Tablet According to Conventional Steps)

After carrying out the sub-coating of uncoated tablets using the sugar-coating liquid of the invention, the tablets were subjected to the smoothing, coloring, finishing and polishing steps using sugar-coating liquids of conventional compositions. The specific embodiments were as follows.

A sub-coating liquid, smoothing liquid and a coloring liquid were prepared by mixing the following components, respectively:

| Sub-coating liquid | |
| --- | --- |
| Sucrose | 37.60 parts by weight |
| Polyvinylpyrrolidone (average Molecular weight: 1,000,000–1,500,000) | 0.37 part by weight |
| Polyethylene glycol 6000 | 4.17 parts by weight |
| Calcium carbonate | 16.70 parts by weight |
| Talc | 8.16 parts of weight |
| Purified water | 33.00 parts by weight |
| Smoothing liquid | |
| Sucrose | 67 parts by weight |
| Purified water | 33 parts by weight |
| Coloring liquid | |
| Sucrose | 57.24 parts by weight |
| Food color Red No. 102 | 0.88 part by weight |
| Food color Red No. 3 | 1.79 parts by weight |
| Purified water | 40.09 parts by weight |

Under identical conditions with those of Example 1, the sub-coating step was repeated 30 times, smoothing step was repeated 3 times and the coloring step, 6 times. Furthermore, finishing coating was repeated twice using the coloring liquid, followed by polishing with carnauba wax and beeswax, to provide a red sugar-coated tablet.

Comparative Example 2

(Preparation of Brown Sugar-coated Tablet According to Conventional Steps)

Comparative Example 1 was repeated except that the food colors Red No. 102 and Red No. 3 which were used in the coloring liquid were replaced with 0.60 part by weight of yellow iron oxide and 0.68 part by weight of iron oxide to provide brown sugar-coated tablet.

Comparative Example 3

(Preparation of Yellow Sugar-coated Tablet According to Conventional Steps)

Comparative Example 1 was repeated except that the food colors Red No. 102 and Red No. 3 used in the coloring liquid were replaced with 3.24 parts by weight of yellow iron oxide, to provide a yellow sugar-coated tablet.

Those colored sugar-coated tablets obtained in the foregoing Examples 2–4 according to the invention and those obtained in Comparative Examples 1–3 according to the conventional process were measured of the relative standard deviation (WCV) as to their weight and degree of unevenness in coloring.

Measuring Method of WCV:

Ten tablets each of the formed sugar-coated tablets were weighed and WCV was calculated by the following equation:

$$WCV(\%) = \frac{\text{standard deviation}}{\text{average value}} \times 100$$

Measuring Method of Unevenness in Coloring:

Unevenness in coloring was measured following the method as described in *Pharmacology*, Vol, 59, pages 43–50 (1999). That is, as to six tablets each of the formed sugar-coated tablets, lightness (L* value) and saturation (a* value, b* value) at the central part of each tablet were measured with color-difference meter, and coloring unevenness (ΔE) was determined by the following equation:

$$\Delta E = [(\Delta L^*)^2 + (\Delta a^*)^2 + (\Delta b^*)^2]^{1/2}.$$

The measured results were as shown in the following Table 1.

TABLE 1

|  | WVC (%) | | Unevenness in color (ΔE) | |
| --- | --- | --- | --- | --- |
|  | This invention | Conventional method | This invention | Conventional method |
| Red sugar-coated tablet | 4.27 | 8.78 | 2.25 | 5.53 |
| Brown sugar-coated tablet | 4.99 | 5.49 | 1.34 | 7.48 |
| Yellow sugar-coated tablet | 6.09 | 6.31 | 2.13 | 8.33 |

As is clear from Table 1, the sugar-coated tablets according to the invention (Examples 2–4) showed less scattering in tablet weight and better evenness in color in comparison with the sugar-coated tablets prepared by the conventional method (Comparative Examples 1–3).

What is claimed is:

1. A monolayer sugar-coated tablet coated with a sugar-coating liquid containing 30–54% by weight of sucrose, 2–10% by weight of polyethylene glycol having an average molecular weight between about 7,300 and 9,300, 0.2–2% by weight of polyvinylpyrrolidone having an average molecular weight between about 1,000,000–1,500,000 and pigment, said tablet having a glossy surface.

2. The monolayer sugar-coated tablet according to claim 1, in which the sugar-coating liquid contains 35–45% by weight of sucrose, 3–5% by weight of polyethylene glycol and 0.3–0.5% by weight of polyvinylpyrrolidone.

3. The monolayer sugar-coated tablet according to claim 1, in which the sugar-coating liquid further contains calcium carbonate and talc.

4. The monolayer sugar-coated tablet according to claim 1, in which the sugar-coating liquid contains 30–33% by weight of water.

5. A process for making monolayer sugar-coated tablet which comprises coating uncoated tablets with the sugar-coating liquid as described in claim 1.

* * * * *